United States Patent [19]

Hickey

[11] Patent Number: 5,570,671
[45] Date of Patent: Nov. 5, 1996

[54] METHOD FOR POSITIONING ESOPHAGEAL CATHETER FOR DETERMINING PRESSURES ASSOCIATED WITH THE LEFT ATRIUM

[75] Inventor: Donald D. Hickey, Amherst, N.Y.

[73] Assignee: The Research Foundation of State University of New York, Buffalo, N.Y.

[21] Appl. No.: 472,786

[22] Filed: Jun. 7, 1995

Related U.S. Application Data

[63] Continuation-in-part of Ser. No. 377,466, Jan. 24, 1995, which is a continuation-in-part of Ser. No. 114,775, Aug. 1, 1993, Pat. No. 5,398,692, which is a continuation of Ser. No. 980,460, Nov. 23, 1992, Pat. No. 5,263,485, which is a continuation-in-part of Ser. No. 717,854, Jun. 25, 1991, Pat. No. 5,181,517, which is a continuation-in-part of Ser. No. 409,041, Sep. 18, 1989, Pat. No. 5,048,532.

[51] Int. Cl.$^6$ .................................................. A61B 5/00
[52] U.S. Cl. .......................... 128/673; 128/687; 128/780; 128/748
[58] Field of Search ..................... 128/668, 672, 128/673, 687, 780, 642, 696, 748; 607/124, 125

[56] References Cited

U.S. PATENT DOCUMENTS

| | | | |
|---|---|---|---|
| 4,134,402 | 1/1979 | Mahurkar | 128/214 |
| 4,214,593 | 7/1980 | Imbruce et al. | 128/748 |
| 4,379,460 | 4/1988 | Judell | 128/671 |
| 4,409,986 | 10/1988 | Apple et al. | 128/715 |
| 4,502,490 | 3/1985 | Evans et al. | 128/780 |
| 4,517,984 | 5/1985 | Perlin | 128/642 |
| 4,706,688 | 11/1987 | Micheal et al. | 128/785 |
| 4,729,384 | 8/1988 | Bazenet | 128/691 |
| 4,850,969 | 7/1989 | Jackson | 604/96 |
| 5,048,532 | 9/1991 | Hickey | 128/780 |
| 5,181,517 | 1/1993 | Hickey | 128/673 |
| 5,191,892 | 3/1993 | Blikken | 128/715 |
| 5,263,485 | 11/1993 | Hickey | 128/673 |
| 5,269,775 | 12/1993 | Bodickey | 604/096 |
| 5,398,692 | 3/1995 | Hickey | 128/673 |

FOREIGN PATENT DOCUMENTS

| | | | |
|---|---|---|---|
| 1069826 | 9/1982 | U.S.S.R. | 604/96 |

OTHER PUBLICATIONS

"We'll meet your needs.", Teleflex Medical/Fluoroplastics, Incorporated, Tall Pines Park, Jaffrey NH 03452.

Hammill and Pritchett, "Simplified Esophageal Electrocardiography Using Bipolar Recording Leads", Annals of Internal Medicine, vol. 95, 1981; pp. 14–18.

Benson, Sanford, Dunnigan and Benditt, "Transesophageal Atrial Pacing Threshold : Role of Interelectrode Spacing, Pulse Width and Catheter Insertion Depth.", American Journal of Cardiology, vol. 53, 1984, p. 63–67.

Lategola and Rahn, A Self–Guiding Catheter for Cardiac and Pulmonary Arteria *Catheterization and Occlusion,* 84 Proc. Soc. Exp. Biol. Med. 667–668 (1953).

Swan, Ganz, Forrester, Marcus, Diamond and Chonette, *Catheterization of the Heart in Man With Use of a Flow--Directed Balloon–Tipped Catheter,* 283:9 The New England J. Med. 447 (1970).

(List continued on next page.)

*Primary Examiner*—Angela D. Sykes
*Assistant Examiner*—Robert L. Nasser, Jr.
*Attorney, Agent, or Firm*—Hodgson, Russ, Andrews, Woods & Goodyear, LLP

[57] ABSTRACT

A method for positioning an esophageal catheter for determining a pressure associated with the left atrium. As a bi-polar electrode is moved up the esophagus, an electrogram is obtained at each of a series of incremental depths. The length of the negative portion of the largest absolute value segment of the respective P wave is determined for at least one P wave in each of the incremental electrograms. The depth of the left atrium is selected to be that which corresponds to the incremental electrode depth at which the electrogram therefor shows the greatest negative portion length. A balloon for determining a pressure associated with the left atrium is positioned at the selected depth.

4 Claims, 5 Drawing Sheets

OTHER PUBLICATIONS

Brown, *A Study of the Esophageal Lead in Clinical Electrocardiography*, American Heart J., vol. 12, No. 1, Jul. 1936, pp. 1–45.

Oblath and Karpman, The Normal Esophageal Lead Electrocardiogram American Heart J., vol. 41, 1951, pp. 369–381.

Arborelius et al, *Hemodynamic Changes in Man During Immersion with Head Above Water*, Aerospace Medicine, Jun. 1972, pp. 592–598.

Brengelmann, Johnson, and Hong, "Electrocardiographic verification of esophageal temperature probe position," Journal of Applied Physiology, vol. 47, 1979, p. 638–642.

Murray, Complications of Invasive Monitoring, 15:2 Medical Instrumentation 85 at p. 89 (Mar. –Apr. 1981).

Robin, Death by Pulmonary Artery Flow–Directed Catheter (editorial), *Time for a Moratorium?*, 92: 4 Chest 727 (Oct. 1987).

H.R. Anderson and P. Pless, Trans–Esophageal Pacing, 6 Pace 674 (Jul.–Aug. 1983).

R.P. Lasser and L. Loewe, *Characteristic Pressure Pulses Records with an Esophageal Ballon in Experimental Mitral Insufficiency Dogs*, Proc. Soc. Experimental Biol. Med. 77:798 (1951).

R.P. Lasser and L. Loewe, Esophageal Pressure Pulse Patterns (*Esophageal Piezocardiogram*), Am. Heart J. 44:531 (1952).

A.C. Taquini, *The Esophageal Pulse Under Normal and Abnormal Conditions*, Am. Heart J. 20:2 (1940).

M. Zoob, *The Esophageal Pulse in Mitral Valve Disease*, Brit. Heart J. 16:39 (1954).

A. J. Gordon, L. Kuhn S. S. Amram, E. Donoso, E. Braunwald, *Left Atrial, "Pumonary Capillary," and Esophageal Ballon Pressure Tracings in Mitral Valve Disease*, Brit, Heart J. 18:327–340 (1956).

Robin, The Cult of the Swan–Ganz Catheter, *Overuse and Abuse of Pulmonary Flow Catheters*, 103:3 Annals of Internal Medicine 445 (Sep. 1985).

Rowley, Clubb, Smith and Cabin, *Right–Sided Infective Endocarditis as a Consequence of Flow–Directed Pulmonary–Artery Catheterization*, 311:18 The New England J. Med. 1152 (Nov. 1, 1984).

J.M. Gore et al., *Handbook of Hemodynamic Monitoring*, 3 (1985).

Gore et al., *A Community–Wide Assessment of Use of Pulmonary Artery Catheters in Patients with Acute Myocardial Infarction*, 92:4 Chest 712–(Oct. 1987).

Baker et al., "Oesophageal Multipurpose Monitoring Probe", Anaesthia, 1983, vol. 38, pp. 892–897.

Nishimura, Katoh, Hanai, and Watanabe, "Optimal Mode of Transesophageal Atrial Pacing", The American Journal of Cardiology, vol. 57, 1986, p. 791–796.

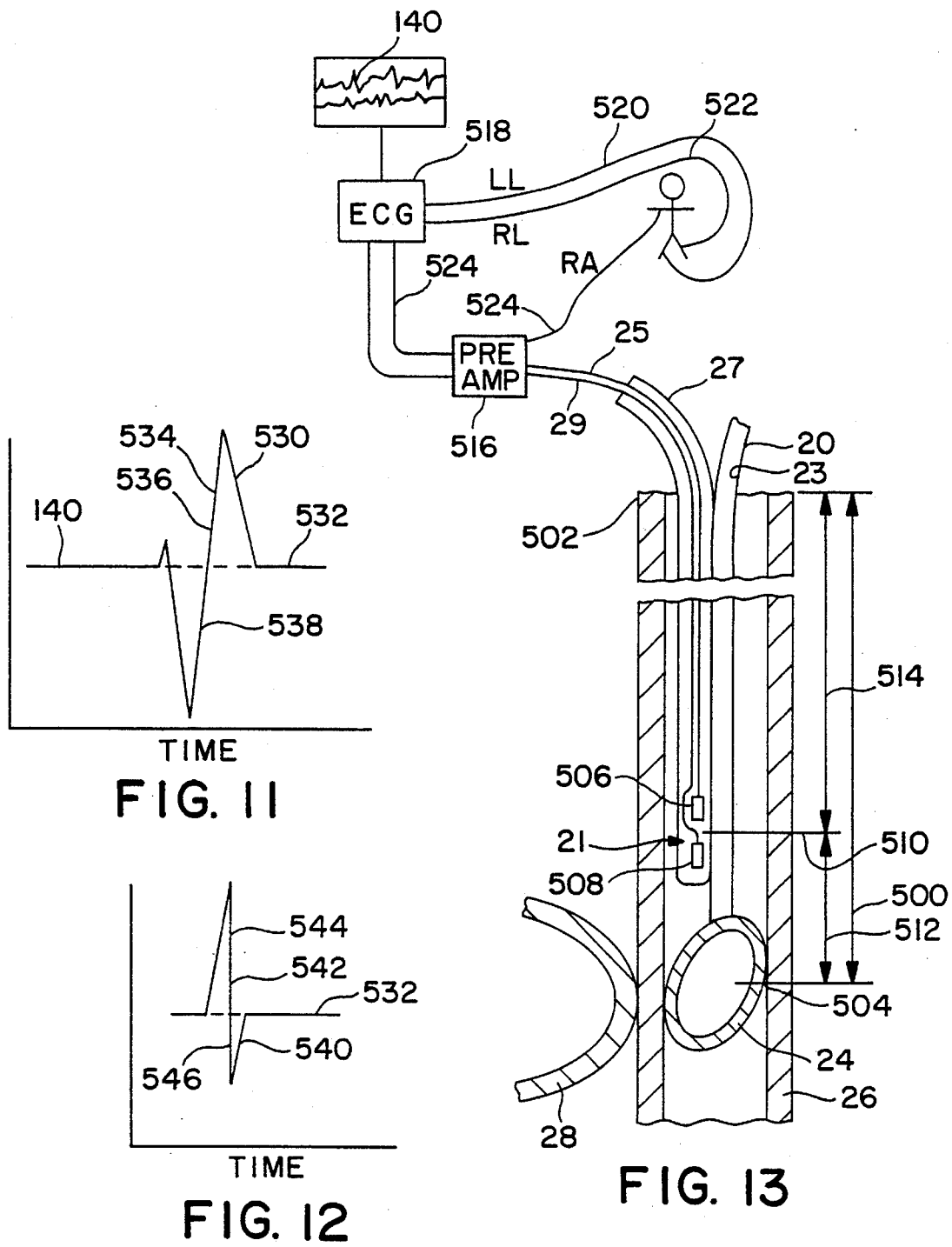

METHOD FOR POSITIONING ESOPHAGEAL CATHETER FOR DETERMINING PRESSURES ASSOCIATED WITH THE LEFT ATRIUM

This is a continuation-in-part of co-pending U.S. patent application Serial No. 08/377,466, filed Jan. 24, 1995, which is a continuation-in-part of U.S. patent application Ser. No. 08/114,775, filed Aug. 31, 1993 (now U.S. Pat. No. 5,398,692), which is a continuation of U.S. patent application Ser. No. 07/980,460, filed Nov. 23, 1992 (now U.S. Pat. No. 5,263,485), which is a continuation-in-part of U.S. patent application Ser. No. 07/717,854, filed Jun. 25, 1991 (now U.S. Pat. No. 5,181,517), which is a continuation-in-part of U.S. patent application Ser. No. 07/409,041, filed Sep. 18, 1989 (now U.S. Pat. No. 5,048,532). The disclosures thereof are hereby incorporated herein by reference.

The present invention relates generally to the quantitative determination of a pressure associated with the left atrium.

In the above patent applications and patents, methods are disclosed for determining pressures such as mean left atrial pressure associated with the left atrium from the effects on an inflated balloon which is inserted in the esophagus so that it is adjacent the left atrium.

The left atrium is adjacent the esophagus over a distance along the esophagus typically of from about 2 to 5 cm. In order to achieve good coupling between the balloon and left atrial pressure, it is considered important to position the balloon within this range along the esophagus over which the left atrium extends so that the predominant pressure acting on the balloon is that of the left atrium.

In connection with pacing, the article "Optimal Mode of Transesophageal Atrial Pacing" by M. Nishimura et al, *American J. of Cardiology*, vol. 57, 1986, p. 791–796, states that "The point showing the largest unipolar atrial electrogram was thus considered the optimal site of pacing for both bipolar and uni-polar stimulation." This article also states that bipolar atrial electrograms should not be used in determining the optimal pacing site. See also "Transesophageal Atrial Pacing Threshold: Role of Interelectrode Spacing, Pulse Width and Catheter Insertion Depth" by D. Benson et al, *American J. of Cardiology*, vol. 53, 1984, p. 63–67. Other articles which may be of interest are "Electrocardiographic Verification of Esophageal Temperature Probe Position" by G. Brengelmann et al, J, *Applied Physiology*, vol. 47, 1979, p. 638–642, and "Simplified Esophageal Electrocardiography Using Bipolar Recording Leads" by S. Hammill et al, *Annals of Internal Medicine*, vol. 95, 1981, p. 14–18.

The method suggested by Nishimura et al may yield good results for pacing. However, in some patients, the electrogram becomes bi-phasic thereby interfering with the ability to determine atrial position merely by determining the point showing the largest unipolar electrogram. The position of greatest absolute P wave amplitude is not always the location of the left atrium for purposes of pressure coupling. Furthermore, the parameters for positioning for pacing are different from those for coupling atrial pressure to an esophageal balloon, where the focus is on determining the location of an electrical site. Thus, a good position for pressure coupling may not be considered to be a good position for pacing. A more accurate and reliable method of determining atrial position for pressure coupling is thus considered to be desirable.

It is accordingly an object of the present invention to provide a more accurate and reliable approach to determining atrial position by means of an esophageal electrode so that pressure values associated with the left atrium may more easily and precisely be obtained.

In order to provide such an accurate and reliable approach, in accordance with the present invention, a series of incremental electrograms are obtained as a bi-polar electrode is moved lengthwise in the esophagus. The length of the negative portion of the largest absolute value segment of the respective P wave is determinated for at least one P wave in each of the incremental electrograms. The esophageal depth for positioning of the inflated balloon is selected to be the depth which corresponds to the incremental electrode depth at which the electrogram therefor shows the greatest negative portion length.

The above and other objects, features, and advantages of the present invention will be apparent in the following detailed description of the preferred embodiment when read in conjunction with the appended drawings wherein the same reference numerals denote the same or similar parts throughout the several views:

BRIEF DESCRIPTION THE DRAWINGS

FIG. 11 and 12 are illustrative views of P waves of electrograms.

Figure 1:
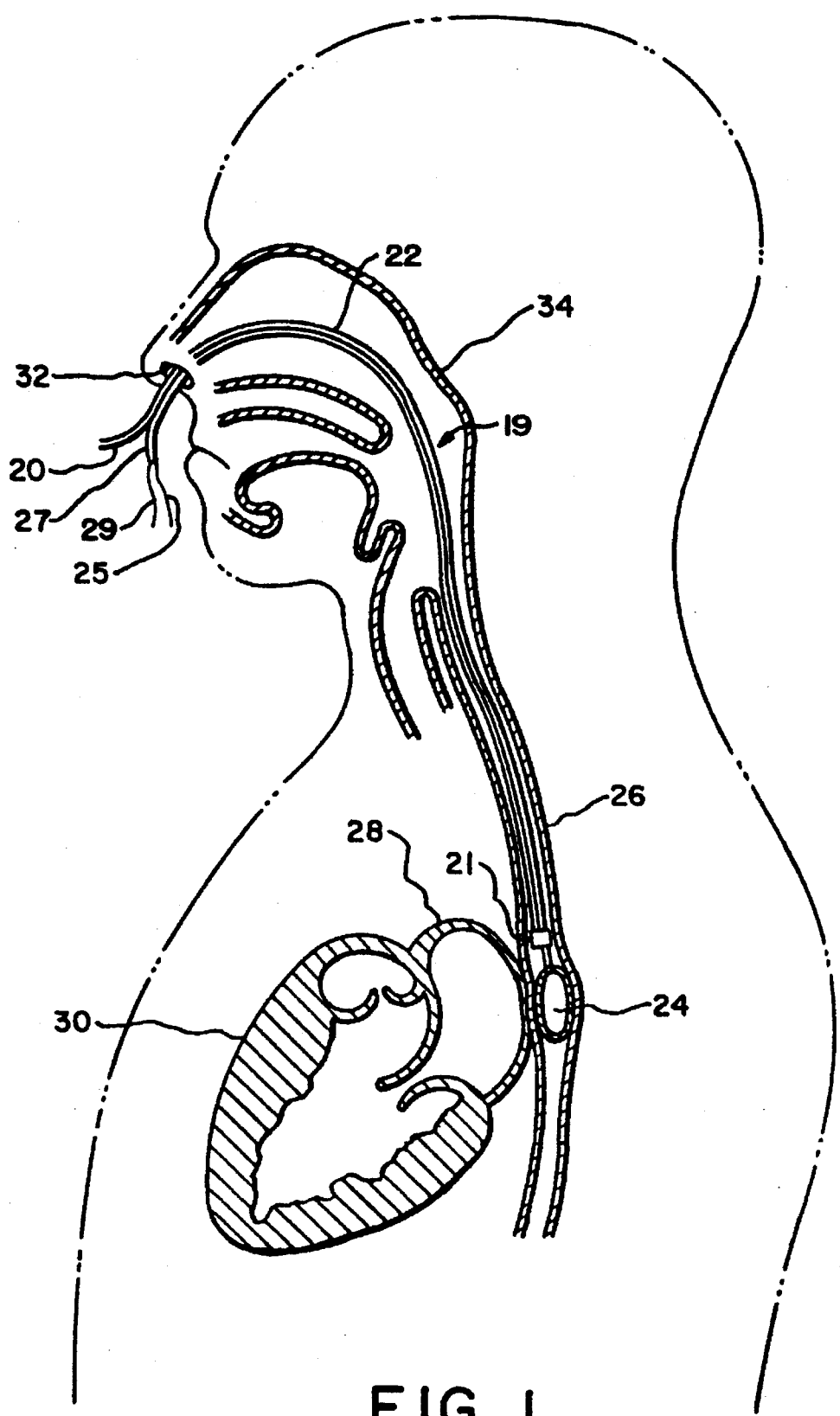
FIG. 1 is a partial left lateral sectional view of the human body taken along the mid-sagittal plane and showing esophageal catheter apparatus including a balloon for determining a pressure associated with the left atrium and an esophageal electrode assembly used in the present invention.

FIG. 13 a detail partial view, partly sectional and partly schematic, of the apparatus of FIG. 1.

DETAILED DESCRIPTION OF THE PREFERRED EMBODIMENT

Referring to FIG. 1, there is illustrated generally at 19 catheter apparatus including a hollow catheter 20 comprising a length of flexible tubing 22 having a bore or lumen 23 (FIG. 13) and on one end of which is attached a balloon 24 for flow communication with the lumen 23 for pressurization of the balloon and for sensing the pressure thereof. An electrode assembly 21 is positioned just above the balloon 24 for obtaining an esophageal electrocardiogram, and a pair of electrical leads 25 and 29, within a second catheter 27, are provided thereto, as will be discussed in greater detail hereinafter.

The balloon 24 is positioned within the esophagus 26 of a human body for the purpose of sensing the pressure of the left atrium 28 of the heart 30. The catheter 20 is inserted balloon first through nasal passage 32, pharynx 34, then into the esophagus 26. If desired, the balloon may alternatively be inserted through the mouth. As shown in FIG. 1, the outer wall of the left atrium 28 is adjacent and essentially in direct contact with the outer wall of the esophagus 26, and advantage is taken of this relationship to determine mean left atrial pressure, transmural pressure, and associated pressures by means of the balloon 24 thusly inserted non-invasively into the esophagus 26 and positioned there along adjacent the left atrium so as to be sufficiently affected thereby to sense left atrial pressure. A more detailed description of the catheter 20, including inflation thereof and pressure measurements thereof, is provided in the aforesaid patents which have issued on the parent applications.

The oscillometric principle is used to determine mean left atrial pressure or a pressure associated therewith by measuring mean pressure in the esophageal balloon 24 as it is gradually inflated while adjacent to the left atrium 28 when the amplitude of balloon pressure oscillations effected by the left atrial pressure is at a peak, as discussed hereinafter. The oscillometric principle is also used to determine mean left atrial pressure or a pressure associated therewith by measuring mean pressure in the inflated balloon 24 when the intensity of a sound wave, after it is transmitted through the balloon, is at a peak, as also discussed hereinafter.

While not wishing to be bound by theory here or elsewhere in this specification, the following is believed to occur as the sensing balloon 24 is pressurized. The gradual filling of the sensing balloon 24 causes the pressure therein to increase at a generally slow steady rate which, in accordance with the theory of the previously discussed oscillometric effect, is affected by the atrial pressure causing oscillations therein as well as by respiratory waves. As the mean balloon pressure approaches the mean left atrial pressure, the atrial pressure oscillations of balloon pressure increase in intensity or amplitude until the balloon pressure resonates maximally, i.e. reaches a peak amplitude, when the mean balloon pressure approximates the mean left atrial pressure. Thereafter, as the mean balloon pressure continues to increase, the amplitude of oscillations due to the atrial pressure decreases. More specifically, the balloon pressure oscillates maximally when its expansion has increased the pressure in the tissue surrounding the left atrium to the point where the mean tissue pressure equals mean left atrial pressure (MLAP). Thus, it may be said that the balloon works best as a pressure transmitter when it is unloaded, i.e., when the mean pressure on both sides of the balloon wall are equal, resulting in the greatest amplitude of balloon pressure oscillations when the mean balloon pressure equals mean left atrial pressure.

Figure 5:
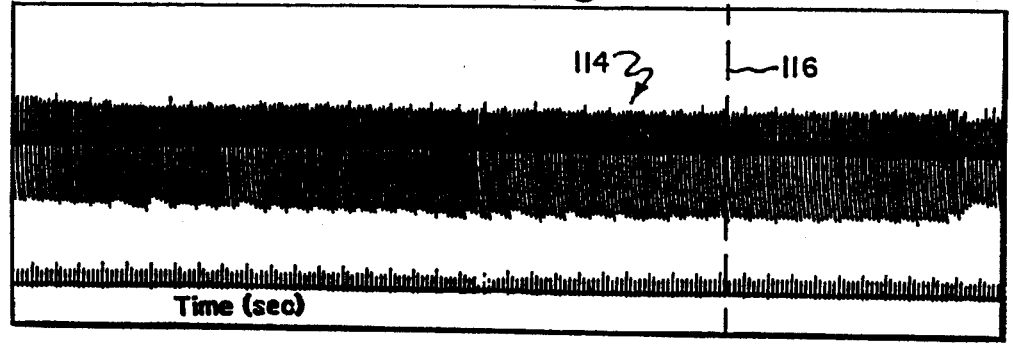
FIG. 5 is a graph of an electrocardiogram taken simultaneously with the pressure traces of FIGS. 2, 3, and 4.

FIGS. 2 to 5 are illustrations of four electronic displays or tracings used to record and display the absolute balloon pressure wave form 108 (FIG. 2), the mean balloon pressure wave form 110 (FIG. 3), the differential signal 112 with added gain from a signal processor (FIG. 4), and a simultaneous electrocardiogram 114 (FIG. 5). Vertical line 116 in each of FIGS. 2 to 5 represents the same point in time. A comparison of the electrocardiograms 140 and 114 in FIGS. 11 and 5 respectively indicates that the time scale for FIG. 11 is greatly expanded relative to the time scale for FIGS. 2 to 5.

By noting the peak resonant amplitude of the wave form 112 (FIG. 4) and comparing it to the simultaneous mean balloon pressure 110 (FIG. 3), the mean left atrial pressure can be determined. Thus, in accordance with the oscillometric principle, the mean balloon pressure approximates the mean left atrial pressure when the oscillations of wave form 112 are at a peak, i.e., the peak or highest amplitude oscillations in the wave form 112 occur at the time 116 when the balloon pressure is equal to mean left atrial pressure. The mean left atrial pressure is thus determined from the example of FIGS. 2 to 5 to be a pressure, illustrated at 128, of about 3 cm water. It should be understood that pressure 128 approximates mean left atrial pressure. To obtain a more precise determination of mean left atrial pressure, the pressure 128 must be adjusted as discussed in the patents which have issued from the aforesaid applications.

Figure 6:
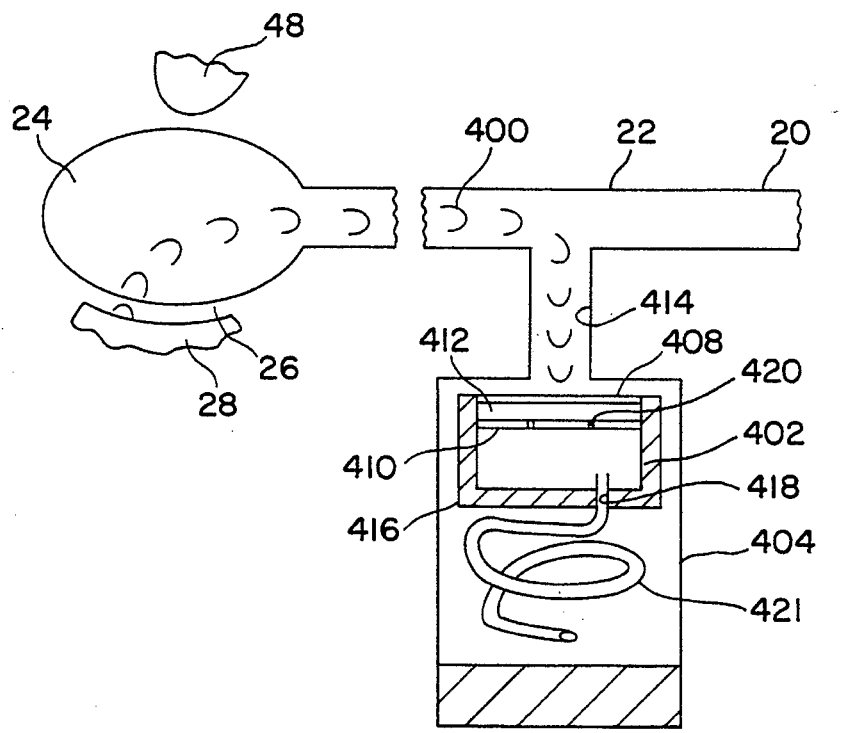
FIG. 6 is a schematic view of apparatus, including the balloon catheter of FIG. 1, in accordance with another embodiment of the present invention.
Figure 7:
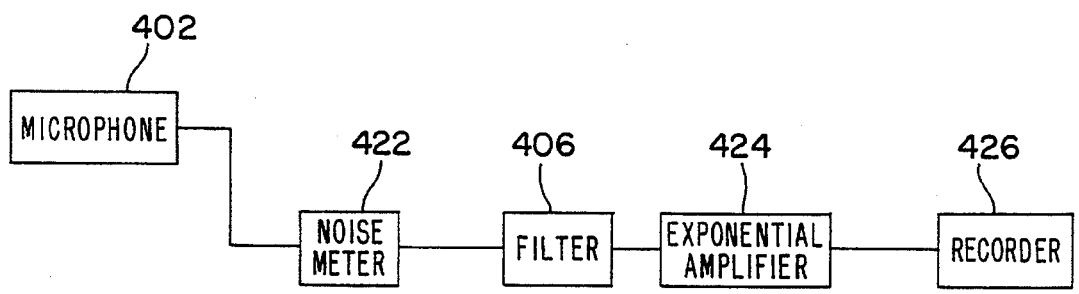
FIG. 7 is a block diagram of electronic components for processing a signal provided by the apparatus of FIG. 6.

Without wishing to be bound by theory here or elsewhere in this application, it is believed that the balloon best transmits not only pressures acting on it but also sound when unloaded, i.e., maximum sound energy may penetrate the balloon wall when it is not in tension (when the pressure on opposite sides thereof is balanced). Thus, the amplitude of heart sounds or any other sounds transmitted through the balloon and tubing is believed to be greatest when the mean balloon pressure equals the mean left atrial pressure (including the effect, if any, of heart weight) so that the balloon is unloaded. Accordingly, referring to FIGS. 6 and 7, in accordance with the present invention, the balloon pressure may be measured when the amplitude (intensity) of heart sounds, illustrated at 400, or other sound waves (sound pressure level) transmitted by the balloon 24 and tubing 22 is at a peak as an indication (after adjustment for the effect, if any, of heart weight) of mean left atrial pressure. Thus, a condenser-type or other suitable microphone, illustrated at 402, is suitably positioned in a suitable housing 404 in an entrance, illustrated at 414, to the tubing 22 to pick up the heart sounds 400, which may then be filtered with a high pass filter, illustrated at 406 in FIG. 7, to remove extraneous frequencies less than perhaps about 30 Hertz. Alternatively, a band pass filter may be used. Thus, the microphone 402 is in pressure or flow communication with the balloon 24 and tubing 22 for receiving the heart sounds 400 passing along the tubing pathway generally free of interference, and the sounds 400 pass through the wall of the balloon 24 on their way to the microphone 402. The microphone 402 may, for example, be an Archer Electret PCmount condenser microphone element marketed by Radio Shack, a division of Tandy Corp., of Fort Worth, Tex. under its catalog no. 270-090.

The condenser microphone 402 conventionally comprises a pair of spaced foil diaphragms 408 and 410 with an air space 412 therebetween. Diaphragm 408 extends across and closes the opening to a sound-blocking housing 416 to receive sound waves 400 passing through entrance 414 from tubing 22. The spaced diaphragms 408 and 410 act as a capacitor with vibration of diaphragm 408 relative to diaphragm 410 effecting a changing capacitance. Diaphragm 410 is positioned within the housing 416 so as to be isolated from the sound so as not to vibrate under the influence of the sound waves 400 as does the diaphragm 408.

Typical applications of a condenser microphone require the pressure on the diaphragms to be equalized. Normally, the pressure changes encountered such as barometric pressure changes or other pressure changes are relatively small and slow so that very small holes in the casing 402 and diaphragm 410 need only be provided. These pressure equilibration holes are accordingly sufficiently small that sound passing into the casing has a very low intensity thus not causing a significant bias effect while allowing slow pressure equilibration in response to slow barometric pressure changes or the like.

The pressure changes within the tubing 22 due to balloon inflation are on the order of 5 or 6 cm. water (5000 to 6000 dynes/cm$^2$) which represents a 1000 to 10,000-fold increase over the pressure changes (perhaps 2 dynes/cm$^2$ for the sound of a truck racing its motor or less than 0.2 dynes/cm$^2$ for heart sounds) typically encountered by the microphone, and these pressure changes due to balloon inflation occur very rapidly. If not adequately simultaneously equilibrated, these pressure changes due to balloon inflation may cause collapse of the condenser. In order to achieve the desired pressure equilibration for the large rapid pressure changes encountered in the tubing 22, a pressure equilibration hole, illustrated at 418, is drilled to a diameter of perhaps about 0.020 inch, and pressure equilibration holes, illustrated at 420, of a suitable size such as 0.0225 inch are drilled in diaphragm 410 so that the pressure in air space 412 is also equalized.

While the hole 418 as well as holes 420 are of a suitable size for pressure equilibration, the hole 418 may be so large as to not sufficiently prevent the passage of sound waves 400 undesirably resulting in a bias effect. In order to substantially reduce the intensity of sound waves 400 passing through pressure equilibration hole 418, a low pass filter comprising a length of micro-bore tubing 421 having an inside diameter of about 0.15 inch is suitably connected to the hole 418. The length of the tubing 421 required to provide adequate pressure equilibration to the microphone yet block the passage of sound was found empirically to be about 6 inches. The tubing 421 is desirably composed of a rigid material such as, for example, polypropylene or a fine glass tube, which sound does not penetrate well.

The balloon and heart pressure wave forms may typically have frequencies in the range of 3 to 9 Hz. In contrast, the frequency of the sound waves 400 may be in the range of 30 to 300 Hz. The microphone 402 is tuned by means of the length of tubing 421 to allow the low frequency pressure changes to equilibrate across the body of the microphone 402 while preventing or substantially retarding the much higher sound frequencies from equilibrating. The lower frequency air pressure changes may accordingly be transmitted with fidelity through the length of the tubing 421, while the high frequency heart sounds 400 may be attenuated resulting in a loss of amplitude to perhaps ⅕ of the original amplitude. Such weakened sound waves passing to the diaphragm 410 should not significantly affect the microphone output. For example, an amplitude of 10 acting on the diaphragm 408 may result in a output amplitude of 8, which is considered to be suitable for obtaining the desired relative sound intensity level to a predetermined base line so that a smooth curve with a pronounced peak may be seen.

The microphone output may be suitably amplified and recorded for use in obtaining a determination of transmural pressure or other pressure associated with the left atrium. However, in order to obtain a more easily usable representation of the sound, referring to FIG. 7, the microphone output is passed through a suitable noise or sound intensity meter 422 in which a decibel equivalent of the sound output is outputted. This decibel equivalent is then filtered by means of filter 406 which removes respiratory frequencies and the like below about 30 Hz. The filtered signal is then passed through a suitable exponential amplifier 424 where it is exponentially amplified to obtain a more pronounced peak. The filtered and amplified signal may then be recorded on a suitable recorder 426.

Figure 2:
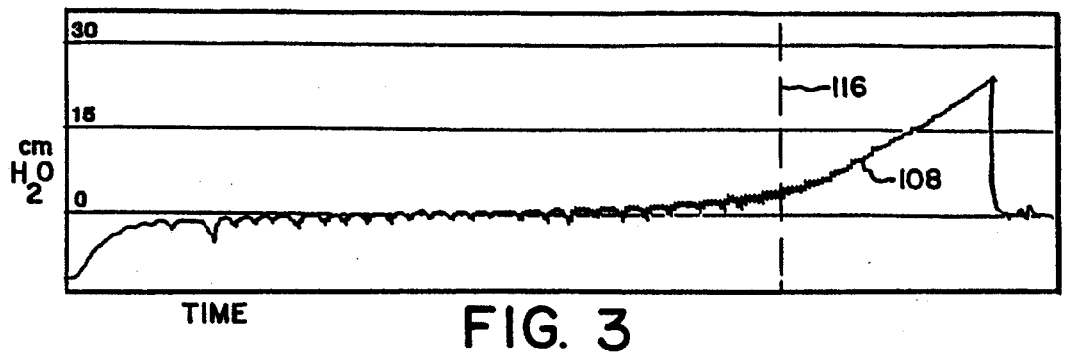
FIG. 2 is a pressure trace of an unfiltered signal of balloon pressure with respiratory and cardiac effected oscillations when the balloon of FIG. 1 is adjacent the left atrium, as the balloon is gradually pressurized in accordance with an embodiment of the present invention.
Figure 3:
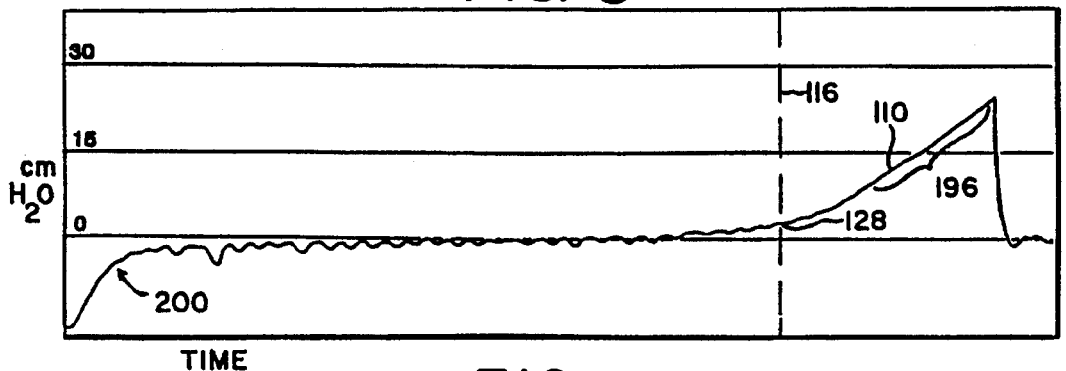
FIG. 3 is a pressure trace of mean balloon pressure for the pressure trace of FIG. 2.
Figure 4:
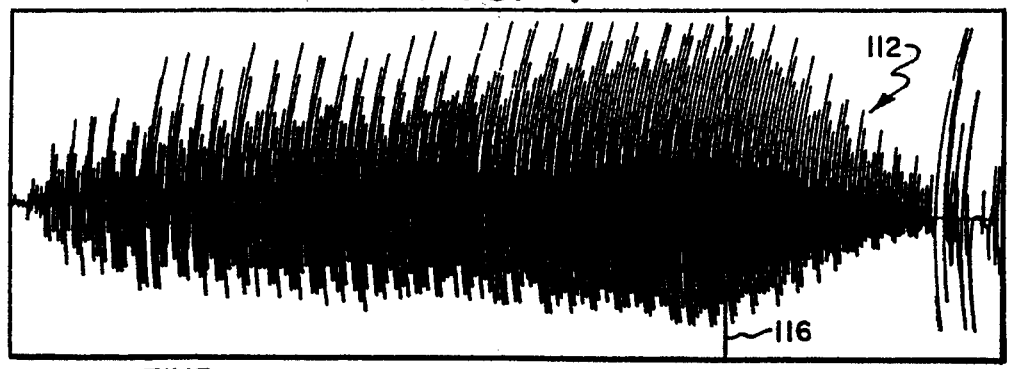
FIG. 4 is a pressure trace of amplified cardiac signal on a steady baseline which signal is derived from the balloon pressure trace of FIG. 2 and covers the same time period as that of FIGS. 2 and 3.
Figure 8:
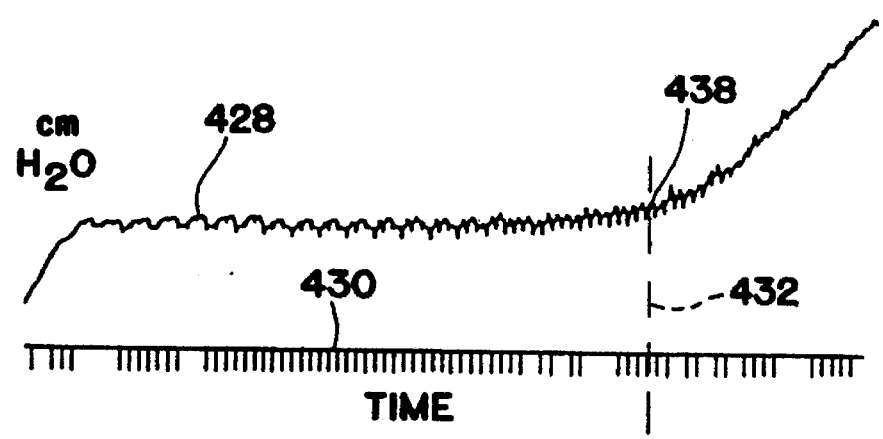
FIG. 8 is a pressure trace similar to that of FIG. 2.
Figure 9:
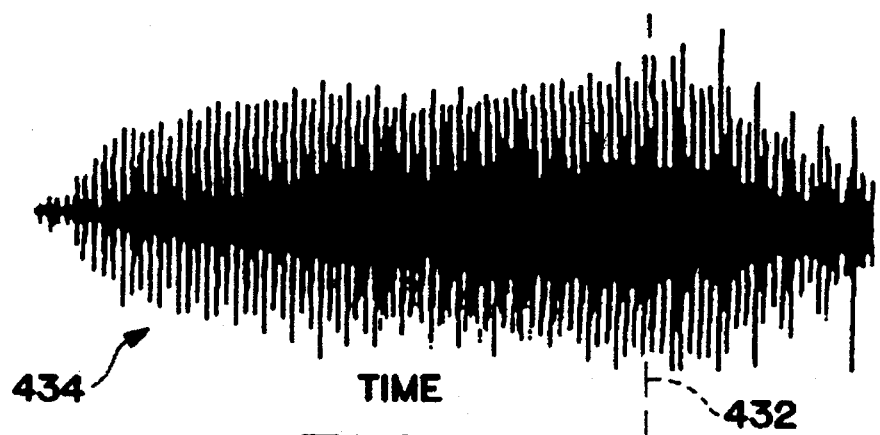
FIG. 9 is a trace of amplified sound output from the apparatus of FIGS. 6 and 7 and covering the same time period as that of FIG. 8.
Figure 10:
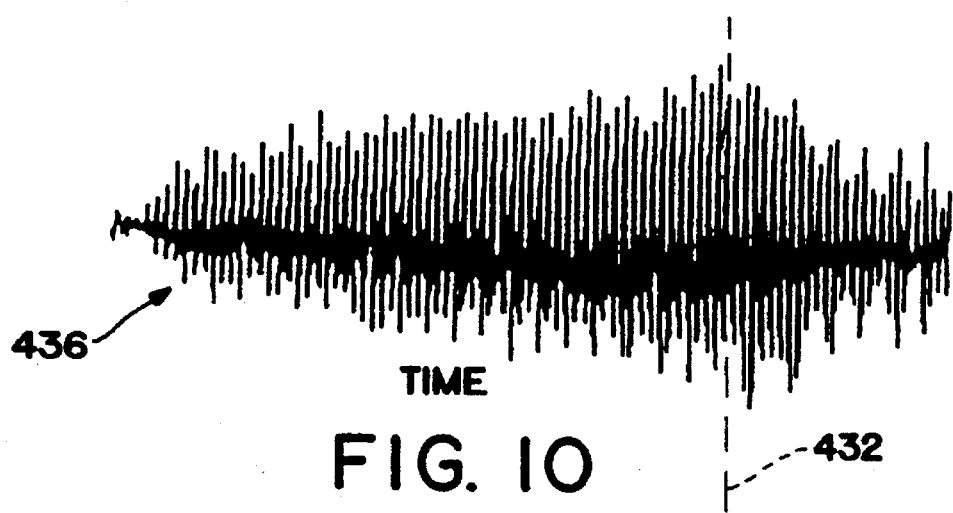
FIG. 10 is a pressure trace similar to that of FIG. 4 which signal is derived from the balloon pressure trace of FIG. 8 and covers the same time period as that of FIGS. 8 and 9.

FIG. 8 shows a tracing 428 similar to that of FIG. 2 of the absolute balloon pressure from the esophageal balloon 24 as it is filled, using a Cobe CDX III transducer. The tracings in FIGS. 8, 9, and 10 occur over the same period of time, as indicated by time line 430. Vertical line 432 in each of FIGS. 8, 9, and 10 represents the same point in time. Tracing 434 in FIG. 9 is the output from the previously described Electret microphone 402 that has been processed through a 10 to 40 Hz band-pass filter. Tracing 436 in FIG. 10 is a steady baseline oscillometric signal from the balloon 24 which is similarly derived as the signal 112 shown in FIG. 4. FIG. 10 shows that the peak resonant amplitude of the balloon pressure signal occurs at time 432. FIG. 9 shows that the intensity (amplitude) of the sound wave 400 has a peak approximately at time 432. Thus, tracing 436 confirms that a tracing 434 of sound waves transmitted through the balloon 24 may also be used to obtain a determination of mean left atrial pressure or other pressure associated therewith. Thus, tracings 434 and 436 each demonstrate a mean left atrial pressure at point 438, assuming no effect by heart weight.

Referring to FIG. 13, in order to obtain a measure of the distance, or esophageal depth, illustrated at 500, from an arbitrary point, illustrated at 502, such as where the catheter exits the nose or mouth to the esophageal location, illustrated at 504, of the left atrium 28 without inaccuracies being introduced by possible bending of the electrode line as it is pushed down the esophagus, the electrode assembly 21 and electrical leads 25 and 29 are suitably enclosed in tubing 27, which is composed of silastic or other suitable material. The tubing 27 is suitably attached to the balloon catheter tubing 20 for movement therewith. However, if desired, the esophageal depth 500 may be determined by use of an electrode catheter which is separate from balloon catheter 20, the electrode catheter 27 thereafter withdrawn, and the balloon catheter inserted to the previously determined depth 500.

In accordance with the present invention, in order to obtain accurate and reliable determinations of esophageal depth 500 easily for positioning of the balloon 24, the esophageal electrode assembly 21 is selected to be bi-polar, i.e., it has two spaced electrodes 506 and 508 which provide signals along leads 25 and 29 respectively. The locus of the composite electrogram signal is considered to be at a point, illustrated at 510, which is midway between the electrodes 506 and 508 when the electrodes are equal in size. If the electrodes are unequal in size, the locus may be determined using principals commonly known to those of ordinary skill in the art to which this invention pertains. This locus 510 is at a distance, illustrated at 512, of perhaps about 2 inches above the balloon 24. Thus, when the esophageal depth 500 to the left atrium 28 has been determined, the balloon 24 may still be below this depth so that it need only be pulled up to this depth 500.

The electrograms, illustrated at 140, may be obtained at increments of perhaps each centimeter as the catheter 27 is pulled up the esophagus so that the esophageal depth 500 may desirably be determined to about the nearest centimeter, the distance for each electrogram being illustrated at 514. However, if desired, the electrograms may be recorded in terms of distance to the center of the first electrode 506, and a distance equal to half of the distance between the electrode centers added thereto.

The signals from the bi-polar electrode 21 are directed to a pre-amplifier, illustrated at 516, which is provided to combine the signals from the individual electrodes 506 and 508 to eliminate baseline wander usually associated with esophageal electrograms, remove low-frequency breathing and other artifacts, and accentuate the P wave while reducing the QRS wave. A suitable pre-amplifier is the Arzco pre-amplifier available from Arzco Medical Electronics, Inc. of Chicago, Ill. which may be used with its Arzco Tapsul pill bi-polar electrode which may be adapted for the present invention. The pre-amplifier 516 couples the combined signal from electrode 21 into a standard electrocardiograph 518, which outputs an esophageal electrogram 140 and to which may be connected left and right leg limb leads 520 and 522 respectively.

The pre-amplifier 516 also provides a right arm limb lead 524 the signal of which is relayed to the electrocardiograph 518 for providing a conventional limb lead II electrogram, which may be of benefit in establishing the P waves in the esophageal electrogram 140. Additional electrograms may be provided, as is commonly known to those to ordinary skill in the art to which this invention pertains.

There is illustrated at 530, in FIG. 11, P wave, representing atrial depolarization and thus related to atrial position, on a steady baseline 532. The portion of an electrogram wave below the base line 532 conventionally is negative while a portion above the base line 532 is conventionally positive. By examining the P wave 530, one can locate a segment, illustrated at 534, which has the greatest absolute deflection or amplitude. This segment 534 is comprised of a positive portion 536, which is above the base line 532, and a negative portion 538, which is below the base line 532. It should be noted that the negative portion 538 preceded the positive portion 536 in the P wave 530. However, in the P wave 540 in FIG. 12, the positive portion 542 of the greatest amplitude segment 544 preceded the negative portion 546.

Based on comparison of esophageal electrograms of persons with x-rays showing their left atrium locations, in accordance with the present invention, a good correlation was found between the known left atrium locations as shown by x-rays and the left atrium locations as determined by selecting the esophageal depth which corresponds to the incremental electrode depth at which the electrogram therefor shows the greatest negative portion length, a negative portion being the negative portion of the segment of the respective P wave which has the largest absolute value.

The esophageal bi-polar electrograms were taken at 1 cm. increments as the electrode catheter was pulled up the esophagus, using a Medtronic coronary sinus implantable pacemaker bi-polar pacing electrode assembly having two electrodes wherein the distance between the centers of the electrodes was 3.3 cms. It should be understood that the distance between electrodes may be different for different bi-polar electrode assemblies.

At each of the increments, the electrogram baseline 532 (the level from which the positive and negative deflections occur) is established so that accurate measurements may be obtained. The segment of each P wave selected with the largest absolute (total) deflection (including negative as well as positive portions) is identified. The length of the negative portion or component of this P wave segment is then measured. Preferably, a number such as perhaps two or three of such negative portion length measurements are made and averaged to provide a measurement for each incremental electrogram. For the purposes of the claims, such an average of negative portion measurements for an incremental electrogram is to be considered to be equivalent to a determined negative portion length for that incremental electrogram. After a measurement is obtained at each increment of distance, the electrode depth is selected which has the largest negative portion or component. This depth is to the center of the upper electrode. Therefore, an amount equal to half of the distance between electrode centers, or 3.3/2 or 1.65 cms., is added to the electrode depth to provide the distance for the selected electrode depth to the center of the bi-polar electrode, which is considered to be the distance to the left atrium. This distance was then compared to the distance to the left atrium as determined by x-ray for the particular person.

The following are the data results on 8 persons showing the distance from the nose to the left atrium as determined by using the method of the present invention with the person in supine positions and as shown by lateral x-rays:

| depth(cm) | neg. portion length (mm) | segment length (mm) |
|---|---|---|
| Number 1 (x-ray is 41.5 to 42.5 cm) | | |
| 44 | −6 | 18 |
| 43 | −9 | 21 |
| 42 | −7 | 14 |
| 41 + 1.65 = 42.65 | −28 | 42 |
| 40 | −21 | 36 |
| 39 | −9 | 34 |
| 38 | −16 | 44 |
| 37 | −15 | 41 |
| 36 | −19 | 46 |
| 35 | −20 | 35 |
| Number 2 (x-ray is 31.5 to 32.5 cm) | | |
| 36 | −1 | 3 |
| 35 | −2 | 5 |
| 34 | −3 | 8 |
| 33 | −3 | 6 |
| 32 | −7 | 8 |
| 31 + 1.65 = 32.65 | −22 | 28 |
| 30 | −10 | 13 |
| 29 | −2 | 15 |
| 28 | −4 | 21 |
| 27 | −6 | 20 |
| Number 3 (x-ray is 37.5 cm) | | |
| 41 | −1 | 5 |
| 40 | −2 | 8 |
| 39 | −1 | 7 |
| 38 | −1 | 4 |
| 37 | −6 | 8 |
| 36 + 1.65 = 37.65 | −14 | 21 |
| 35 | −5 | 12 |
| 34 | −3 | 11 |
| 33 | −2 | 10 |
| 32 | −2 | 10 |
| 31 | −2 | 6 |
| 30 | −1 | 4 |
| Number 4 (x-ray is 36 to 37 cm) | | |
| 42 | −4 | 6 |
| 41 | −8 | 10 |
| 40 | −7 | 8 |
| 39 | −3 | 6 |
| 38 | −3 | 11 |
| 37 | −3 | 12 |
| 36 + 1.65 = 37.65 | −10 | 18 |
| 35 | −4 | 12 |
| 34 | −2 | 10 |
| 33 | −5 | 9 |
| 32 | −6 | 9 |
| 31 | −4 | 6 |

| depth | neg. portion length (mm) | segment length (mm) |
|---|---|---|
| Number 5 (x-ray is 40.5 cm) | | |
| 47 | −1 | 2 |
| 46 | −2 | 4 |
| 45 | −3 | 10 |
| 44 | −3 | 11 |
| 43 | −3 | 14 |
| 42 | −1 | 7 |
| 41 | −13 | 16 |
| 40 | −15 | 18 |

-continued

| | | | |
|---|---|---|---|
| 39 | 39.5 + 1.65 = 41.15 | −15 | 18 |
| 38 | | −7 | 10 |
| 37 | | −4 | 10 |
| 36 | | −5 | 15 |
| 35 | | −2 | 8 |
| 34 | | −3 | 7 |
| 33 | | −3 | 5 |
| Number 6 (x-ray is 39 to 40 cm) | | | |
| 46 | | −3 | 9 |
| 45 | | −2 | 7 |
| 44 | | −4 | 14 |
| 43 | | −4 | 15 |
| 42 | | −5 | 16 |
| 41 | | −3 | 9 |
| 40 | | −4 | 5 |
| 39 | | −20 | 27 |
| 38 | 38.5 + 1.65 = 40.15 | −20 | 28 |
| 37 | | −18 | 24 |
| 36 | | −7 | 9 |
| 35 | | −3 | 8 |
| 34 | | −4 | 11 |
| 33 | | −3 | 7 |
| Number 7 (x-ray is 34.5 to 35.0 cm) | | | |
| 42 | | −2 | 4 |
| 41 | | −3 | 5 |
| 40 | | −5 | 16 |
| 39 | | −1 | 12 |
| 38 | | −8 | 20 |
| 37 | | −7 | 19 |
| 36 | | −5 | 15 |
| 35 | | −5 | 9 |
| 34 | | −12 | 15 |
| 33 | | −18 | 23 |
| 32 | + 1.65 = 33.65 | −20 | 29 |
| 31 | | −7 | 21 |
| 30 | | −10 | 15 |
| 29 | | −4 | 10 |
| 28 | | −5 | 12 |
| 27 | | −4 | 8 |
| Number 8 (x-ray is 37.5 cm) | | | |
| 44 | | −3 | 6 |
| 43 | | −3 | 5 |
| 42 | | −2 | 4 |
| 41 | | −3 | 5 |
| 40 | | −4 | 4 |
| 39 | | −1 | 5 |
| 38 | | −5 | 17 |
| 37 | | −6 | 19 |
| 36 | + 1.65 = 37.65 | −7 | 20 |
| 35 | | −6 | 17 |
| 34 | | −6 | 13 |
| 33 | | −3 | 6 |
| 32 | | −5 | 6 |
| 31 | | −3 | 5 |
| 30 | | −2 | 4 |

(note: data in the 39 to 42 cm. range may not have been reliable)

It should be noted that in Numbers 5 and 6, there were two depths having the greatest negative portion length. As indicated, the depth in such a case is taken to be midway between the two depths.

The method of the present invention determined left atrial position in all of the above cases within 1 cm., which is considered adequate for balloon placement. The use of the longest P wave segment length to determine left atrial depth correlated with the results in only 7 of the above cases thus indicating its unreliability, unlike the showing of reliability for the method of the present invention.

In should be understood that, while the present invention has been described in detail herein, the invention can be embodied otherwise without departing from the principals thereof. Such other embodiments are meant to come within the scope of the present invention as defined by the appended claims.

What is claimed is:

1. A method for determining a pressure associated with the left atrium comprising the steps of (a) moving a bi-polar electrode lengthwise within the esophagus, (b) obtaining an electrogram at each of a series of incremental depths as the electrode is moved lengthwise within the esophagus, (c) determining for at least one P wave in each of the incremental electrograms the length of the negative portion of the largest absolute value segment of the respective p wave, (d) selecting an esophageal depth which corresponds to the incremental electrode depth at which the electrogram therefor shows the greatest negative portion length, (e) inserting a balloon into the esophagus, (f) positioning the balloon at the selected esophageal depth, (g) inflating the balloon, and (h) determining a pressure associated with the left atrium from effects on the inflated balloon at the selected esophageal depth.

2. A method according to claim 1 wherein the step of determining the pressure comprises measuring the balloon pressure when the amplitude of balloon pressure oscillations when the balloon is at the esophageal depth and effected by the left atrial pressure is at a peak.

3. A method according to claim 1 wherein the step of determining the pressure comprises measuring the balloon pressure when the intensity of a sound wave is, after the sound wave is transmitted through the balloon, at a peak.

4. A method according to claim 1 wherein the step of obtaining a series of electrograms comprises obtaining electrograms at about 1 cm. increments as the electrode is pulled up the esophagus.

\* \* \* \* \*

UNITED STATES PATENT AND TRADEMARK OFFICE
CERTIFICATE OF CORRECTION

PATENT NO. : 5,570,671
DATED : November 5, 1996
INVENTOR(S) : Donald D. Hickey

It is certified that error appears in the above-identified patent and that said Letters Patent is hereby corrected as shown below:

On the title page:

Item [63]
Title Page, Related U.S. Application Data - line 2, "Aug. 1" should be --Aug. 31--.

Col. 1, line 44 - "J," should be --J.--.

Col. 9, between lines 34 and 35 - insert --(note: data in the 39 to 42 cm. range may not have been reliable)--.

Col. 9, last line - delete "(note: data in the 39 to 42 cm. range may not have been reliable)".

Signed and Sealed this

Fifteenth Day of July, 1997

Attest:

BRUCE LEHMAN

*Attesting Officer*   *Commissioner of Patents and Trademarks*